United States Patent [19]

Schultz et al.

[11] Patent Number: 5,346,509
[45] Date of Patent: Sep. 13, 1994

[54] PROCESS FOR DYEING HAIR BY THE SEQUENTIAL TREATMENT OF HAIR WITH METAL ION-CONTAINING COMPOSITION AND WITH A DYE COMPOSITION CONTAINING 5,6-DIHYDROXYINDOLE-2-CARBOXYLIC ACID AND CERTAIN DERIVATIVES THEREOF

[75] Inventors: Thomas M. Schultz, Highland Mills, N.Y.; Keith C. Brown, New Canaan; Leszek J. Wolfram, Stamford, both of Conn.; Giuseppe Prota, Napoli, Italy

[73] Assignee: Clairol Incorporated, Stamford, Conn.

[21] Appl. No.: 46,462

[22] Filed: Apr. 14, 1993

Related U.S. Application Data

[63] Continuation of Ser. No. 846,966, Mar. 6, 1992, abandoned, which is a continuation of Ser. No. 629,181, Dec. 21, 1990, abandoned, which is a continuation of Ser. No. 371,697, Jun. 23, 1989, abandoned, which is a continuation of Ser. No. 193,389, May 12, 1988, abandoned.

[51] Int. Cl.$^5$ ............................................. A61K 7/13
[52] U.S. Cl. ............................................. 8/423; 8/429; 8/623; 8/624; 8/626; 8/628
[58] Field of Search .................. 8/423, 429, 623, 624, 8/625, 626, 628, 629, 634

[56] References Cited

U.S. PATENT DOCUMENTS

| | | | |
|---|---|---|---|
| 2,934,396 | 4/1960 | Charle et al. | 8/423 |
| 3,194,734 | 7/1965 | Seemuller et al. | 8/423 |
| 3,215,605 | 11/1965 | Soloman | 8/432 |
| 3,993,436 | 11/1976 | Fujinuma | 8/423 |
| 4,173,453 | 11/1976 | Shiah | 8/405 |
| 4,195,972 | 4/1980 | Lapidus | 8/405 |
| 4,208,183 | 6/1980 | Grollier et al. | 8/609 |
| 4,822,375 | 4/1989 | Lang et al. | 8/423 |
| 4,885,006 | 12/1989 | Grollier et al. | 8/423 |
| 4,961,754 | 10/1990 | Grollier | 8/423 |
| 5,064,442 | 11/1991 | Grollier | 8/423 |
| 5,112,360 | 5/1992 | Garoche et al. | 8/423 |
| 5,131,911 | 7/1992 | Lang et al. | 8/429 |

FOREIGN PATENT DOCUMENTS

| | | |
|---|---|---|
| 271186 | 1/1987 | European Pat. Off. |
| 239826 | 10/1987 | European Pat. Off. |
| 2028818 | 12/1970 | Fed. Rep. of Germany |
| 1439307 | 4/1966 | France |
| 1233210 | 9/1989 | Japan |
| 2132642 | 7/1984 | United Kingdom |
| 2187456 | 9/1987 | United Kingdom |
| 2197885 | 6/1988 | United Kingdom |
| 2207153 | 1/1989 | United Kingdom |
| 2207443 | 1/1989 | United Kingdom |

OTHER PUBLICATIONS

Chem. Abstract No. 53(16):15169i, Abstract of Bouchilloux et al., Compt. rend. vol. 247 pp. 2484–2486 (1958); abstract published Aug. 1959.

Chem. Abstract No. 55(13):12490i, Abstract of Bouchilloux et al., Bull. Soc. Chim. Biol., vol. 42, pp. 1045–1064 (1960); abstract published Jun. 1961.

Chem. Abstract No. 60(6):6810c Abstract of Piatelli et al., Tetrahedron vol. 19 No. 12 pp. 2061–2072 (1963); abstract published Mar. 1964.

Chem. Abstract No. 64(4):5032h Abstract of Benigni et al., J. Heterocyclic Chem., vol. 2 No. 4, pp. 387–392 (1965); abstract pub. Feb. 1966.

The Science of Hair Care ed. Charles Zuiak pub. Marcel Dekker, Inc., N.Y., 1986*, pp. 276–278.

Primary Examiner—Linda Skaling
Attorney, Agent, or Firm—Charles J. Zeller

[57] ABSTRACT

Process for dyeing human hair by the sequential treatment of the hair with a metal ion and particularly transition metal ion containing composition and with a dye composition containing 5,6-dihydroxyindole-2-carboxylic acid.

8 Claims, No Drawings

PROCESS FOR DYEING HAIR BY THE SEQUENTIAL TREATMENT OF HAIR WITH METAL ION-CONTAINING COMPOSITION AND WITH A DYE COMPOSITION CONTAINING 5,6-DIHYDROXYINDOLE-2-CARBOXYLIC ACID AND CERTAIN DERIVATIVES THEREOF

This is a continuation of U.S. Ser. No. 07/846,966 filed Mar. 6, 1992, now abandoned, which is a continuation of U.S. Ser. No. 07/629,181 filed Dec. 21, 1990, now abandoned, which is a continuation of U.S. Ser. No. 07/371,697 filed Jun. 23, 1989, now abandoned, which is a continuation of U.S. Ser. No. 07/193,389 filed May 12, 1988, now abandoned.

BACKGROUND OF INVENTION

This invention relates to processes and compositions for dyeing hair and particularly for dyeing hair on the human head. More particularly, it concerns the use of 5,6-dihydroxyindole-2-carboxylic acid (sometimes referred to herein as DHICA) in such processes and compositions.

Efforts have been made in the past to provide a hair dyeing process that mirrors the formation of hairs' natural pigment—melanin. These efforts relied in general upon treatment of hair with a recognized intermediate of the melanin pathway—5,6-dihydroxyindole—DHI.

While the melanin formation can be successfully achieved by this approach, the results have left much to be desired. Firstly, DHI is a highly unstable compound and this presents considerable difficulty in product formulation. Secondly, the colors obtained on hair with DHI tends to be achromatic and thus require separate treatments to attain a broader range of shades.

Indeed color modulation of dihydroxyindole dyed hair has been taught to require either a pretreatment of the hair with a color modifier such as a metal ion, or iodide or a reducing agent prior to dye application. Alternatively, an oxidative posttreatment can be effectively used to the hair. Moreover, precursors such as 5,6-dihydroxyindole require a complicated synthesis which makes the use of this material expensive and often precludes its commercial use. The present invention eliminates the aforesaid disadvantages.

THE INVENTION

It has now been unexpectedly found that DHICA may be employed to dye hair with soft shades of brown that emulate the naturally occurring melanin type pigments. Such dyeings use a process which involves sequentially treating hair with a metal ion, and particularly a transition metal ion containing composition, and with a hair dye composition containing DHICA. Hair dyed in accordance with the process of the present invention has a natural lustre and sheen without a coated feel. Moreover the dyeouts have proven to have good light- and wet-fastness; that is to say, the dyeings obtained are photo- and shampooing-stable.

As used herein the term "sequentially treating" means that the metal ion containing composition and the DHICA containing compositions are applied one after the other without specifying which is to be applied first. In accordance with the present invention either order of application may be used; that is, the metal ion-containing compositions may be applied first followed by the application of the DHICA-containing compositions, or vice versa.

PRIOR ART

There is ample patent history on the use of synthetic organic compounds which purport to mimic the natural coloring process in man. In the 1950's Raper and Mason (R. A. Nicolaus, "Melanins", in *Chemistry of Natural Compounds*, E. Lederer, ed., Herman Publishers, Paris, 1970), detailed a mechanism which accounted for the transformation of L-DOPA (3,4-dihydroxyphenylanine) to eumelanin, the primary coloring agent in man. The material was formed by oxidation of L-DOPA to DOPACHROME (a reddish material in solution) followed by conversion to either 5,6-dihydroxyindole ( DHI ) or 5,6-dihydroxyindole-2-carboxylic acid (DHICA). Subsequent oxidation of either DHI or DHICA ultimately yields the eumelanin. The entire process is regulated in-vivo by the enzyme tyrosinase.

It has been revealed recently that the Raper-Mason scheme for eumelanogenesis is incomplete and that a crucial component has been omitted. It now is apparent that the biological transformation of L-DOPA to DHI is not singular and it involves, rather, the additional formation of 5,6-dihydroxyindole-2-carboxylic acid, DHICA (S. Ito, *Biochim. Biophys. Acta*, 883, 155–161 [1986]). Indeed it was proposed by Swan in the 1970's that natural eumelanin was a mixed polymer incorporating DHI, DHICA, and L-DOPA (G. A. Swan, *Zeitschrifte Natur. d. Org. Chem.*, "The Chemistry, Biochemistry, and Structure of Melanins", 152–186; 1976).

Several patents teach that the above process is mimicked by reaction of L-DOPA or tyrosine with an animal or vegetable tyrosinase and will dye hair a permanent black color (U.S. Pat. No. 2,539,202, U.S. Pat. No. 2,875,769, U.S. Pat. No. 3,993,436, and JP 54110337). In addition, certain catalysts have been found effective in accelerating the dyeing of human hair: JP 53133641, JP 50130443, JP 8056159, U.S. Pat. No. 4,390,341, U.S. Pat. No. 4,453,941, EP 1610773A, and SU 566895 all teach that when L-DOPA and its derivatives are contacted with a metal-ion salt the reaction to dye hair brown or black will be accomplished much more readily. Several patents also teach that hair may be dyed using DHI either in conjunction with or serially applied with an oxidizing agent: U.S. Pat. No. 2,934,396, DE 1083505, U.S. Pat. No. 3,194,734, U.S. Pat. No. 4,208,183, DE 2820193, and NL 8304157A. One of the major deficiencies in using DHI has been that the material is highly reactive and requires the utmost care both in its preparation and in its use, for it will spontaneously react to form granular materials which are ineffective in coloring hair.

The other drawback in DHI coloring systems, important from the color aesthetes, is the very limited range of hues than can be obtained. The dyeouts achieved via DHI use are primarily achromatic with the color intensity varying between black and grey, typically lacking warm brown or auburn tones without the addition of certain non-melanogenic materials.

In light of this, it was surprising to find that DHICA effectively dyes human hair and skin. DHICA is a naturally occurring material that can now be used to dye hair soft shades of brown. The hair has a natural lustre and sheen without the coated feeling typical of hair dyed with conventional permanent hair colorants.

It has thus been very surprising to find that DHICA can be effectively employed either alone or in mixture with DHI to provide a wide range of hair colors displaying a range of brown tonalities. Another advantage of DHICA is its ease of preparation (one step synthesis; H. Sobotha & J. Austin; *J. Am. Chem., Soc.;* 73, p. 3077); and chemical stability during storage. We find that hair dyed with DHICA-containing compositions retains its luster and sheen without the raspy feel frequently observed in the case of conventional hair colorants.

All references cited are hereby incorporated by reference unless stated otherwise.

DETAILED DESCRIPTION OF INVENTION

The DHICA containing hair dye compositions of this invention may take any of a variety of forms. They may be made up into, e.g., gels, lotions, creams, aerosol compositions or the like or into simple emulsions, suspensions or solutions. One form that has been found to be useful is a solution of DHICA in a solvent system that is preferably an aqueous-organic solvent system. In such solutions, the organic solvent, which is preferably an alcohol, constitutes from about 1% to 99% by volume of the solvent system, the balance generally being of water. In the preferred forms of this invention the organic solvent will constitute between about 5% to about 30% by volume of the solvent system and the water will comprise between 95% to 70% also on a volume basis.

A variety of organic solvents may be employed in the solvent system of the DHICA dye compositions of this invention. As indicated above alcoholic solvents have been found to be quite useful, especially those containing $C_1$ to $C_6$ alkanols and $C_1$ to $C_6$ ethers of such alkanols. By way of illustrating the solvents that are useful for the present purposes mention may be made of the following: ethanol, n-propanol, iso-propanol, ethoxyethanol, etc.

The quantity of DHICA that will be contained in the hair dye compositions of this invention may vary over a range depending on the results desired and the other ingredients contained in the composition, including other hair coloring agents. All that is required is that an effective hair dyeing quantity of DHICA be incorporated in the hair dye compositions. Generally, this quantity will fall within the range of from about 0.001% to about 10.0% by weight of DHICA based on the total weight of the hair dye composition, with the preferred concentration being from about 0.01% to about 5% on the same weight basis. Optimally, the DHICA concentration is about 1% by weight on the same weight basis.

This invention is not limited to DHICA proper. Such derivatives as the alkyl, aryl, or benzyl esters may be similarly employed (Structure I) to provide a source of the DHICA moiety during the hair dyeing process. Additionally N-substituted derivatives I, ($R_1$=alkyl, aryl, or benzyl) may also be useful. It would be expected that such analogs of DHICA dye hair similarly but different from those taught for DHI and N-methyl-DHI. Indeed in the use of these latter two compounds color modulation of the dyeouts to light browns must be effected by incorporating into the process a bleaching agent as described in U.S. Pat. No. 3,194,734. It is apparent that N-substitution of the indole only slightly changes the shade and addition of other agents is required to alter the tonal quality of the dyeout.

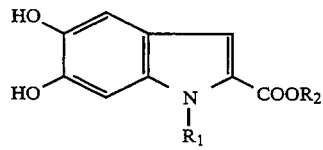

$R_1, R_2$ = H, alkyl, aryl, or benzyl

The pH of the DHICA-containing hair dye compositions can also vary over a range depending on the other ingredients in the composition and the results desired. Usually the pH of the composition will be from about 3 to about 10, the optimum pH being from about 3 to about 8.

It is sometimes advantageous to use a dihydroxyindole (DHI) in admixture with DHICA in the hair dye composition of this invention. This provides the possibility of obtaining a wider range of colors on the hair. When a dihydroxyindole is employed it may vary in concentration depending on the quantity of the other ingredients contained in the composition and/or the results described. Generally, it will be present in the range from about 0.01% to about 4.0% by weight based on the total weight of the hair dye composition, with the preferred range being from about 0.5% to about 2.0% on the same weight bases.

A variety of dihydroxyindoles may be used for this purpose. By way of example mention may be made of dihydroxyindole (DHI), N-methyldihydroxyindole ($CH_3NDHI$), and the like. Generally, N-substitutued DHI's in which the substituents are $C_1$ to $C_6$ alkyl groups and substituted or unsubstituted aryl groups are preferred.

Any of a number of adjuvants may also be added to the present DHICA hair dye compositions. These may be added to facilitate the application of the dye composition to the hair, to improve the chemical or physical stability of the composition, to modify the color obtained in the dyeout or to improve the organoleptic properties of the composition. To these ends the DHICA hair dye composition may contain surfactants, foaming agents, metal scavengers, antioxidants, preservatives, auxiliary hair coloring agents, thickening agents, perfumes, product coloring agents, other solvents, etc.

The metal ion containing compositions used in this invention may contain any of a wide variety of metal ions which will usually be ions of a transition metal. These are chosen so as to provide a deposit of metal ion on the hair which will promote, accelerate or catalyze the formation of melanin-like pigments from DHICA and, if present, from a dihydroxyindole. Among the preferred metal ions to be present in the metal ion containing compositions employed in this invention the following may be mentioned: $Cu^{+2}$, $Zn^{+2}$, $Mn^{+2}$, $Co^{+2}$, $Fe^{+2}$, $Cr^{+3}$ $Fe^{+3}$, $Mo^{+2}$ and $Ti^{+2}$. These may be incorporated in the present metal ion composition in the form of salts that are preferably water soluble salts. The anions of said salts again might be quite varied. These include such anions as the sulfate, acetate, nitrate, lactate and citrate anions.

The vehicle of the metal ion containing compositions will usually be an aqueous vehicle in which the metal ions are in solution. The concentration of the metal ions need only be sufficient to complex with hair to promote, accelerate or catalyze the pigment formation from the DHICA. Generally this concentration will be in the range of from about 0.0004M to about 1.0M with the optimum concentration being about 0.04M.

It may be sometimes advantageous to employ one or more reducing agents to modulate the dyeout color obtained with the DHICA compositions utilized in this invention. A variety of reducing agents may be used for this purpose. By way of exemplification of suitable reducing agents, mention may be made of the dithionites (e.g., alkali metal dithionites), bisulfites (e.g. alkali metal or alkaline earth metal bisulfites), thioglycollates (e.g. ammonium, alkali metal or alkaline earth metal thioglycollates), etc.

When a reducing agent is used in the practice of the present invention it may be used alone in a carrier (e.g. an aqueous carrier) or as part of the composition containing the metal ions or the DHICA, either alone or in admixture with a dihydroxyindole. In any event, the concentration of the reducing agent in these compositions may vary and generally will be in the range of from about 0.01% to about 3.0% by weight based on the total weight of the composition in which it is contained the preferred concentrations being from about 0.01% to about 2% on the same weight basis.

The reducing agent may be applied in any of a number of fashions. Thus it may be applied as an independent step from a composition that contains none of metal ions, DHICA or DHI. In this case, it may proceed or follow the application of the metal ion containing composition. It may also be applied before or after the application of the DHICA/DHI composition. Similarly, when contained in the DHICA/DHI containing composition it may be applied before or after the application of the metal ion composition.

In a preferred aspect of this invention, the reducing agent will constitute part of the metal ion containing composition and will be employed as a pretreatment before the application of the DHICA composition.

When it is desired to lighten the obtained dyeouts, this can be accomplished by subjecting the colored hair resulting from the above described process to the action of an oxidizing or reducing agent. A variety of such agents are known in the hair dye art which are suitable for the purpose. These are exemplified by such oxidizing agents as $H_2O_2$, persulfates, or reducing agents such as sulfites.

The oxidizing or reducing agent will generally be applied from a composition containing the same which ordinarily will be an aqueous composition. The concentration of such agents in the lightening composition may vary somewhat but for the most part will be in the range of from about 0.001% to about 5.00% by weight based on the total weight of the composition in which it is contained.

In carrying out the process of the present invention the hair will be treated with the various compositions in amounts sufficient to thoroughly wet the hair. The metal ion composition may be applied over a range of time periods which will generally be from about 5 to about 30 minutes with the optimum treating time being about 10 minutes. This time of metal ion composition contains a reducing agent. The application of the metal ion composition will take place at about room temperature although somewhat elevated temperatures may also be employed.

The application of the DHICA composition may also take place over a range of time periods with the usual time period being in the range of from about 5 to about 60 minutes, the optimum time period being about 10 minutes. The DHICA composition will also usually be applied at ambient temperatures but again somewhat elevated temperatures can be employed.

When used separately the reducing composition will be applied over a time range of from about 5 to about 30 minutes.

Following the application of the treatment compositions employed in the present process the hair will ordinarily be rinsed with water and blow-dried.

The following examples are given to further illustrate this invention. It is understood, however, that this invention is not limited thereto.

A summary of solution preparations is followed by Table I which gives the colors obtainable using said solutions on blended grey hair. Table II summarizes the effects of post-treatment of dyed hair with either alkaline peroxide or persulfate solutions.

EXAMPLES

General methods of preparation of buffers, metal salt solutions, indole dye compositions, reducing agent solutions and peroxide solutions.

1. Buffer solutions;
    (a) pH 3—one gram of sodium phosphate (Na $H_2PO_4.H_2O$) is dissolved in 100 ml of water and to this is added 0.85 ml of phosphoric acid ($H_3PO_4$) to give a 0.07 m pH 3 phosphate buffer.
    (b) pH 5—one gram of sodium acetate ($NaOCOCH_3$) and 1.2 ml of acetic acid are mixed into 100 ml of water to give a 0.12M pH 5 acetic acid buffer.
    (c) pH 7—one gram of sodium phosphate ($NaH_2PO_4.H_2O$) and seventeen hundred milligrams of dibasic phosphate ($Na_2HPO_4$) are mixed together into 100 ml of water to give a pH 7 0.11M phosphate buffer.
    (d) pH 8—one ml of monoethanolamine ($NH_2CH_2CH_2OH$) is added to 100 ml of water and 0.2 ml of 6N HCl added to give a 0.1M pH 8.1 buffer.
    (e) pH 9—one ml of monoethanolamine ($NH_2CH_2CH_2OH$) is added to 100 ml of water to give a 0.1M pH 9.3 buffer.
2. Metal Salt Solutions;
    (a) Copper (II) Sulfate—one gram of copper sulfate-pentahydrate ($CuSO_4.5H_2O$) is dissolved in 100 ml of pH 9 buffer to give 0.04M $Cu^{+2}$.
    (b) Zinc (II)—0.5 gm of zinc sulfate.heptahydrate ($ZnSO_4.7H_2O$) is dissolved in 100 ml of pH 8 buffer or pH 5 buffer to give a 0.03M solution of $Zn^2$.
    (c) Iron (II)—0.7 gm of ferrous acetate [Fe(O-$COCH_3$)$_2$] is dissolved in pH 5 buffer (100 ml) to give a 0.04M $Fe^{+2}$ solution.
3. Indole Dye Compositions
    (a) DHICA—0.1 gm of 5,6-dihydroxyindole-2-carboxylic acid (DHICA) is dissolved in 3.0 ml of 95% ethanol and this is added portion-wise to 7.0 ml of a buffer solution to give 1% DHICA at the appropriate pH.
    (b) NCH$_3$DHI/DHICA—0.5 gm of 5,6-dihydroxy-N-methylindole (NCH$_3$DHI) and 0.05 gm DHICA are dissolved together in 3.0 ml of 95% ethanol and then this is added portion-wise to pH 9 buffer to give a 0.5% NCH$_3$DHI/0.5% DHICA (wt/wt) dye composition. Other wt % composition mixtures of NCH$_3$DHI/DHICA are prepared similarly.

(c) DHI/DHICA—0.05 gm of DHICA in 3.0 ml of 95% ethanol is added 0.01 gm of 5,6-dihydroxyindole and this solution is added portionwise to 7.0 ml of pH 9 buffer to give a 0.5% DHICA/0.1% DHI dye composition. Other wt % DHICA/DHI compositions are prepared similarly.

4. Post-treatment Solutions (a) 3% $H_2O_2$—50 ml of 20 volume hydrogen peroxide is added to 40 ml of water along with 10 ml monoethanolamine to give a pH 9.2 solution.

(b) 1% Sodium Dithionite—1.0 gm of sodium dithionite ($Na_2S_2O_4$) is added to 100 ml of pH 5 buffer to give a 1% solution.

(c) 1% ammonium thioglycollate—1.7 ml of a 60% ammonium thioglycollate solution ($NH_4CO_2CH_2SH$) is added to 98.3 ml of pH 8 buffer to give a 1% solution.

TABLE I

A Summary of Dyeouts on Blended Grey Hair Using a Process of Applying Sequentially for 5 and 15 Minutes Respectively a Metal-salt and Indole Dye Composition on Hair
pH values refer to that of the indole or metal-ion solution of each step

| Indole Composition | $Zn^{+2}$ | $Zn^{+2}$ + Dithionite | $Zn^{+2}$ + Thioglycollate | $Fe^{+2}$ | $Fe^{+2}$ + $Cu^{+2}$ | $Cu^{+2}$ |
|---|---|---|---|---|---|---|
| 1% DHICA at pH 7 | Ex. 1<br>pH 8<br>yellow-gold | Ex. 2<br>pH 5<br>light ash brown | Ex. 3<br>pH 8<br>light brown | Ex. 4<br>pH 5<br>light golden brown | | |
| 1% DHICA at pH 5 | | | | | Ex. 5<br>pH 9<br>dark golden brown | Ex. 6<br>pH 9<br>light golden brown |
| 1% DHICA at pH 9 | | | | | | Ex. 7<br>pH 7<br>golden-yellow brown |
| 0.8% DHICA + 0.2% NCH3DHI at pH 9 | | | | | | Ex. 8<br>pH 9<br>warm golden brown |
| 0.5% DHICA + 0.5% NCH3DHI at pH 9 | Ex. 10<br>pH 8<br>pale golden brown | | | | | Ex. 9<br>pH 9<br>medium brown |
| 0.5% DHICA + 0.1% DHI at pH 9 | | | | Ex. 11<br>pH 5<br>dark golden brown | | Ex. 12<br>pH 9<br>dark brown |
| 0.8% DHICA + 0.4% DMI at pH 9 | | Ex. 13<br>pH 8<br>dark golden brown | | | | Ex. 14<br>pH 9<br>very dark brown |

TABLE II

Effects of Post-treating Metal-salt/DHICA Dyed Hair with Oxidants

| Metal-salt/Indole Combination | Post-Treatment 3% pH 9 $H_2O_2$ | 1% Persulfate pH 5 |
|---|---|---|
| 1% DHICA/$Cu^{+2}$ as per Ex. 7 | Ex. 15<br>Before: golden-yellow brown<br>After: very pale golden brown | Ex. 16<br>Before: golden yellow brown<br>After: light gold |
| 0.8% DHICA/plus 0.4 DHI/$Cu^{+2}$ as per Ex. 14 | Ex. 17<br>Before: very dark brown<br>After: light golden brown | |
| 0.5% DHICA/0.5% NCH3DHI/$Cu^{+2}$ | Ex. 18<br>Before: medium brown<br>After: light golden | |
| as per Ex. 9 | brown | |

Reasonable variations, such as those which would occur to a skilled artisan, can be made herein without departing from the scope of the invention.

What is claimed:

1. A process for dyeing human hair a brown color, the process consisting of the steps set forth below:
   (a) applying to the hair an aqueous buffered hair dye composition having a pH of from about 3 to about 10, said hair dye composition consisting essentially of from about 0.01 to about 5% by weight of a colorant having the structure:

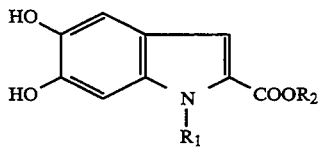

wherein $R_1$ is hydrogen, benzyl or an alkyl of from 1 to 6 carbon atoms and $R_2$ is hydrogen, benzyl or an alkyl substituent group;
   (b) applying an aqueous composition consisting essentially of a transition metal ion selected from the group consisting of $Cu^{+2}$, $Fe^{+2}$, $Fe^{+3}$, $Co^{+2}$, $Mn^{+2}$ and $Ti^{+2}$ to the hair for a period of time sufficient to deposit on the hair an amount of said metal ion effective to promote the conversion of the colorant of structure I to a melanin-type pigment, said step (a) being conducted before or after the conduct of step (b), and (c) optionally rinsing the hair with water following steps (a) and (b), the hair following the completion of the process having a brown color tone.

2. The process of claim 1 wherein the concentration of the metal ion in said aqueous composition is such as to effect said deposit in not more than about 10 minutes.

3. The process of claim 1 or 2 wherein the transition metal ion is $Cu^{+2}$.

4. The process of claim 1 wherein the colorant of structure I is 5,6-dihydroxyindole-2-carboxylic acid.

5. The process of claim 1 wherein the colorant of structure I is 5,6-dihydroxyindole-2-carboxyalkyl ester.

6. The process of claim 1, 4 or 5 wherein step (b) is conducted in advance of step (a).

7. The process of claim 1, 4 or 5 wherein step (a) is conducted in advance of step (b).

8. The process of claim 1, 4 or 5 wherein the hair dye composition further contains 5,6-dihydroxyindole.

* * * * *